United States Patent [19]

Prahl et al.

[11] 4,327,727

[45] May 4, 1982

[54] COLLECTING BAG FOR ARTIFICIAL INTESTINAL OUTLETS

[75] Inventors: Jan Prahl, Rullstorf; Franz Gelbenegger, Hamburg-Volksdorf, both of Fed. Rep. of Germany

[73] Assignee: Ipos Gesellschaft für integriert Prothesen-Entwicklung und orthopädietechnischen Service GmbH & Co., KG, Lüneburg, Fed. Rep. of Germany

[21] Appl. No.: 169,724

[22] Filed: Jul. 17, 1980

[30] Foreign Application Priority Data

May 10, 1980 [DE] Fed. Rep. of Germany ....... 3017989

[51] Int. Cl.³ .............................................. A61F 5/44
[52] U.S. Cl. ............................................... 128/283
[58] Field of Search ........ 128/283, 294, 295, DIG. 24

[56] References Cited

U.S. PATENT DOCUMENTS

| 2,703,576 | 3/1955 | Furr, Jr. ..................... 128/283 |
| 3,373,745 | 3/1968 | Benfield et al. ............. 128/283 |
| 3,522,807 | 8/1970 | Millenbach .................. 128/283 |
| 3,618,606 | 11/1971 | Brown et al. ............... 128/283 |

FOREIGN PATENT DOCUMENTS 215015 10/1909 Fed. Rep. of Germany ...... 128/283

Primary Examiner—C. Fred Rosenbaum
Attorney, Agent, or Firm—Toren, McGeady and Stanger

[57] ABSTRACT

The invention relates to a collecting bag for artificial intestinal outlets. It ensures an optimum stoma provision and has an adhesive surface integrated into the collecting bag surface. Thus, a high adhesive strength is obtained when the collecting bag is in use and as a result absolute security is given to the wearer or carrier of the bag, even when vigorous movements are performed.

5 Claims, 2 Drawing Figures

COLLECTING BAG FOR ARTIFICIAL INTESTINAL OUTLETS

BACKGROUND OF THE INVENTION

The invention relates to a collecting bag with a connecting opening for artificial intestinal outlets constructed in self-adhesive manner in the marginal area thereof.

For use in conjunction with artificial intestinal outlets or so-called anus praeter or stoma a number of different constructions of collecting bags made from liquid-tight and odour-impermeable foil material for receiving the intestinal elimination products are known and these can be connected in different ways to the human body. In one known construction, the collecting bag is stuck directly to the body in the vicinity of the artificial intestinal outlet. For this purpose, adhesive foils are used but these foils have a pronounced tendency to crease, so that liquid and moisture can trickle through the creases formed and cause skin irritations which only head slowly. As an alternative, sealing rings are used which are made from a highly plastic, purely tropical wood rosin, called karaya gum, which does not have a high adhesive power and does not provide a strong connection to the skin of the body.

BRIEF SUMMARY OF THE INVENTION

The problem of the invention is to provide a collecting bag for artificial intestinal outlets which permits an optimum stoma provision, which adapts to all the unevennesses in the stoma area, which has a high degree of sealing, in which the adhesive surface is integrated into the collecting bag surface and which provides absolute security even when the person carrying or wearing it performs vigorous movements.

According to the invention, this problem is solved by a collecting bag for artificial intestinal outlets of the type described hereinbefore, wherein in the vicinity of the peripheral edge of the connecting opening, a circular adhesive material with an aproximately central bottleneck-like narrowing is provided in the upper foil of the collecting bag and which at its non-adhering lateral surfaces is surrounded by the upper foil whilst retracting the latter into the bottleneck-like narrowing.

The disadvantages of the prior art collecting bags are obviated by the collecting bag according to the invention. The adhesive material used for the present collecting bag and which in particular comprises castable, addition-crosslinked, skin-compatible silicone rubber adapts more readily to all the unevennesses in the stoma area than the adhesive foils hitherto used on such bags. In addition, the addition-crosslinked silicone rubber used has a high adhesive power. Due to its integration in the upper foil of the collecting bag, the specific shape of the adhesive material elastically absorbs the tensile stress of the foil when the bag is full. Tearing away between foil and adhesive material is not possible. As the adhesive material is integrated into the collecting bag foil through a corresponding pre-shaping of the upper foil of the bag by deep drawing, the adhesive surface of the adhesive material comes to rest in the plane formed by the collecting bag upper foil, so that a very firm engagement of the said upper foil in the skin is ensured. The specific shaping of the adhesive material as a result of the bottleneck-like narrowing permits a firm seat and maximum securing of the position of the adhesive material in the upper foil of the collecting bag, so that even under high tensile stress with the bag full, the adhesive material cannot lift from the upper foil of said bag.

Further advantageous developments of the invention can be gathered from the subclaim. The development of claim 3 is particularly advantageous in which towards the tensioned side of the collecting bag the adhesive material has a portion which is wider than the rest of said material, so that in the area of the bag subject to greatest tensile stress, there is a firm engagement of the bag to the skin. Additionally, a collecting bag constructed in this way is easier to handle, particularly for elderly people than a bag with the known adhesive fixtures.

BRIEF DESCRIPTION OF THE DRAWINGS

The invention is described in greater detail hereinafter relative to a non-limitative embodiment and the attached drawings.

DETAILED DESCRIPTION OF THE PREFERRED EMBODIMENTS

Figure 1:
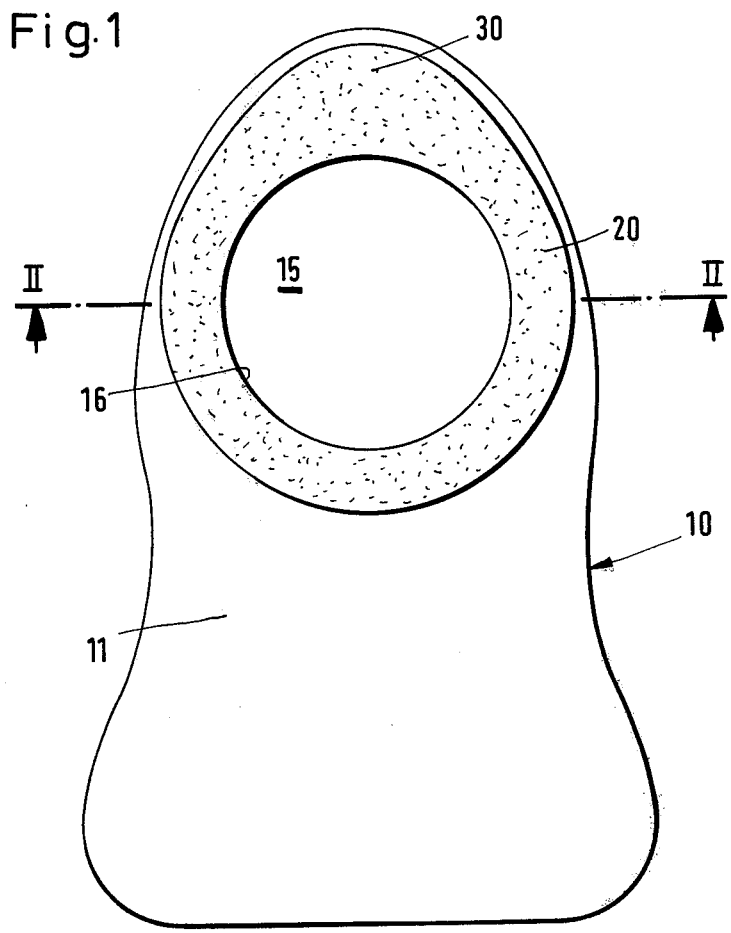
FIG. 1 a view of a collecting bag with its connecting opening.
Figure 2:
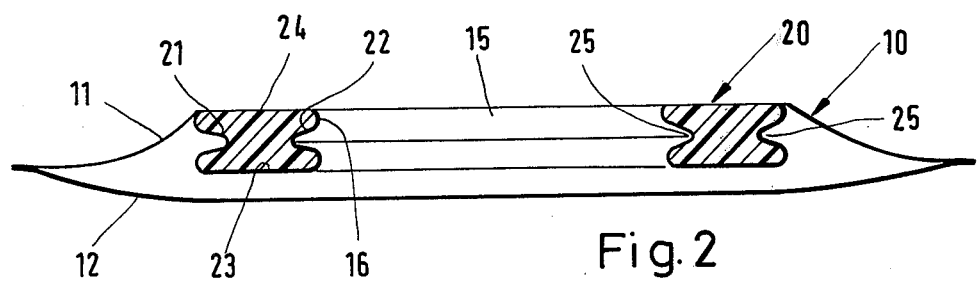
FIG. 2 a larger scale vertical section along the line II—II of FIG. 1.

The collecting bag 10 of FIGS. 1 and 2 has a double-wall construction and comprises an upper foil 11 and a lower foil 12 welded together by their edges. Collecting bag 10 is made from a liquid-tight and odour-impermeable plastic foil. The shape and dimensions of the collecting bag 10 can be selected at random.

A connecting opening 15, which is circular or can have some other suitable geometrical configuration is made in the upper foil 11 of collecting bag 10 for connecting the latter to an artificial intestinal outlet. The peripheral edge of said connecting opening 15 is designated by the following reference numeral 16 (FIG. 1).

In the vicinity of the peripheral edge 16 of connecting opening 15, a circular adhesive material 10 is introduced into the upper foil 11 of connecting bag 10 in such a way that, with the exception of the upper adhesive surface designated 24, all the lateral surfaces 21, 22 and 23 are surrounded by the foil material. The shape of the adhesive material 20 corresponds to the geometrical shape of the connecting opening 15. This circular adhesive material 20 is formed from a castable, addition-crosslinked, skin-compatible silicone rubber. In order to be able to anchor this adhesive material 20 in the upper foil 11 of collecting bag 10 the adhesive material 20, which preferably has a square or rectangular cross-section, is provided with a neck-like narrowing 25 in the vicinity of its two lateral surfaces 21, 22 (FIG. 2). Such a circular adhesive material 20 is inserted into the upper foil 11 of collecting bag 10 is brought about by the foil material of upper foil 11 being given a shape, preferably by a deep-drawing process in the insertion area for adhesive material 20 which corresponds to the profile of the latter. The adhesive material 20 inserted in upper foil 11 is then tightly surrounded by the foil material of upper foil 11 up to its upper adhesive surface 20, i.e. foil 11 is adapted to the contours predetermined by the profile of adhesive material 20. Thus, a firm seat of the adhesive material 20 in upper foil 11 is ensured, particularly due to the course of foil 11 in the vicinity of the neck-like retraction or narrowing 25 of adhesive material 20. Adhesive material 20 is inserted in upper foil 11 of the collecting bag 10 in such a way that the upper adhesive surface 24 of material 20 comes to rest in the plane formed by the upper foil 11, so that between adhesive surface and foil 11 no step-like shoulder is formed.

Preferably, a small quantity of a skin-caring silicone oil is added to the adhesive material 20.

As shown in FIG. 1, adhesive material 20 has a widened portion 30 towards the tensioned side. Due to this construction of adhesive material 20, very good adhesion between the latter and the skin is ensured in the tensioned area of collecting bag 10. Due to the widened portion 30 of adhesive material 20 the surface area is increased and therefore so is the adhesion of the bag to the body.

What is claimed is:

1. A collecting bag of the type adapted to be attached to the body of a wearer for receiving therein bodily discharge comprising: two sheets arranged in a generally overlapping relationship sealed together at the peripheral edges thereof, one of said sheets constituting a body-side sheet of said bag adapted to be located adjacent the body of a wearer when said bag is in use, said body-side sheet having an annular edge portion defining an opening therethrough; and an annular attachment member connected to said body-side sheet about said opening for adhesively affixing said bag to the body of a wearer; said annular attachment member defining an intake orifice through which bodily discharge may enter said bag, an annular generally planar pressure-sensitive adhesion surface facing outwardly of said bag surrounding said intake orifice adapted to be adhered to the body of a wearer, said planar adhesion surface being defined between a radially innermost annular edge and a radially outermost annular edge, and a remainder surface portion located on the opposite side of said annular attachment member inwardly of said bag and extending continuously between said innermost and outermost annular edge; said body-side sheet being connected with said annular attachment member with said annular edge portion in adhesive contact with said remainder surface portion; said annular edge portion extending to completely cover said remainder surface portion continuously from said innermost edge to said outermost edge so that the outer surface of said body-side sheet extends contiguously with said outermost edge along the entire length thereof.

2. A collecting bag according to claim 1, wherein said annular adhesion surface has a widened portion towards one side of the collecting bag.

3. A collecting bag according to claim 1, wherein said annular attachment member is made from an addition-crosslinked, skin-compatible silicone rubber which has a pleasant feel.

4. A collecting bag according to claim 1 wherein said remainder surface portion is formed with at least one concavity extending completely around said annular attachment member and wherein said annular edge portion extends in surface contact with said remainder surface portion within said at least one concavity.

5. A collecting bag according to claim 4 wherein two concavities are formed in said remainder surface portion having said annular edge portion in surface contact therein.

* * * * *